United States Patent
Tuck et al.

(10) Patent No.: US 6,239,292 B1
(45) Date of Patent: May 29, 2001

(54) PROCESS FOR PREPARING GAMMA-BUTYROLACTONE, BUTANE-1,4-DIOL AND TETRAHYDROFURAN

(75) Inventors: Michael William Marshall Tuck, London; Michael Anthony Wood, Middlesbrough; Andrew George Hiles, Chesham Bois, all of (GB)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/554,194

(22) PCT Filed: Nov. 2, 1998

(86) PCT No.: PCT/GB98/03264

§ 371 Date: Jun. 28, 2000

§ 102(e) Date: Jun. 28, 2000

(87) PCT Pub. No.: WO99/25678

PCT Pub. Date: May 27, 1999

(30) Foreign Application Priority Data

Nov. 13, 1997 (GB) .................................................. 9724004

(51) Int. Cl.$^7$ .................................................. C07D 305/12
(52) U.S. Cl. ........................... 549/326; 549/508; 568/864
(58) Field of Search ....................... 549/326, 508; 568/864

(56) References Cited

U.S. PATENT DOCUMENTS

| | | | |
|---|---|---|---|
| 2,638,481 | 5/1953 | Nachod, Jr. .................... | 260/533 |
| 2,893,924 | 7/1959 | Courtier ............................ | 202/42 |
| 3,040,059 | 6/1962 | Hoyte ............................ | 260/346.4 |
| 3,818,680 | 6/1974 | Marquis .......................... | 55/48 |
| 3,850,758 | 11/1974 | Smith et al. .................... | 203/38 |
| 3,891,680 | 6/1975 | Katsumoto et al. ......... | 260/346.8 M |
| 4,071,540 | 1/1978 | Marquis ........................ | 260/346.76 |
| 4,118,403 | 10/1978 | White ............................. | 260/346.76 |
| 4,584,419 | 4/1986 | Sharif et al. ..................... | 568/881 |
| 4,751,334 | 6/1988 | Turner et al. ...................... | 29/136 |
| 4,767,869 | 8/1988 | Harrison et al. .................. | 549/295 |
| 4,795,824 | 1/1989 | Kippax et al. .................... | 560/204 |
| 4,919,765 | 4/1990 | Wilkes et al. ...................... | 203/64 |
| 4,945,173 | 7/1990 | Wood .............................. | 549/295 |
| 5,254,758 | 10/1993 | Hiles et al. ....................... | 568/881 |
| 5,310,954 | 5/1994 | Hiles et al. ....................... | 549/429 |

FOREIGN PATENT DOCUMENTS

| | | |
|---|---|---|
| 1125014 | 4/1955 | (FR) . |
| 2 285 386 | 4/1976 | (FR) . |
| 727828 | 4/1955 | (GB) . |
| 763339 | 12/1956 | (GB) . |
| 768551 | 2/1957 | (GB) . |
| 35-7460 | 1/1930 | (JP) . |
| 32-8408 | 8/1930 | (JP) . |
| WO 86/03189 | 6/1986 | (WO) . |
| WO 88/00937 | 2/1988 | (WO) . |
| WO 90/03127 | 4/1990 | (WO) . |
| WO 90/08127 | 7/1990 | (WO) . |
| WO 91/01960 | 2/1991 | (WO) . |
| WO 97/43242 | 11/1997 | (WO) . |

OTHER PUBLICATIONS

6001 Chemical Abstracts, Columbus, Ohio, U.S., vol. 52 (1958) Sep. 10; No. 17.

*Primary Examiner*—Bernard Dentz
(74) *Attorney, Agent, or Firm*—Nixon & Vanderhye P.C.

(57) ABSTRACT

A process for the production of at least one $C_4$ compound selected from 1,4-butanediol, gamma-butyrolactone and tetrahydrofuran, in which a solution of maleic anhydride in a high boiling ester is esterified with a $C_1$ to $C_4$ alcohol to form the corresponding maleate ester which is hydrogenated to form the at least one $C_4$ compound. The specified high boiling ester has a boiling point which is about 30 degrees C. higher than that of the di-($C_1$–$C_4$ alkyl)maleate.

25 Claims, 1 Drawing Sheet

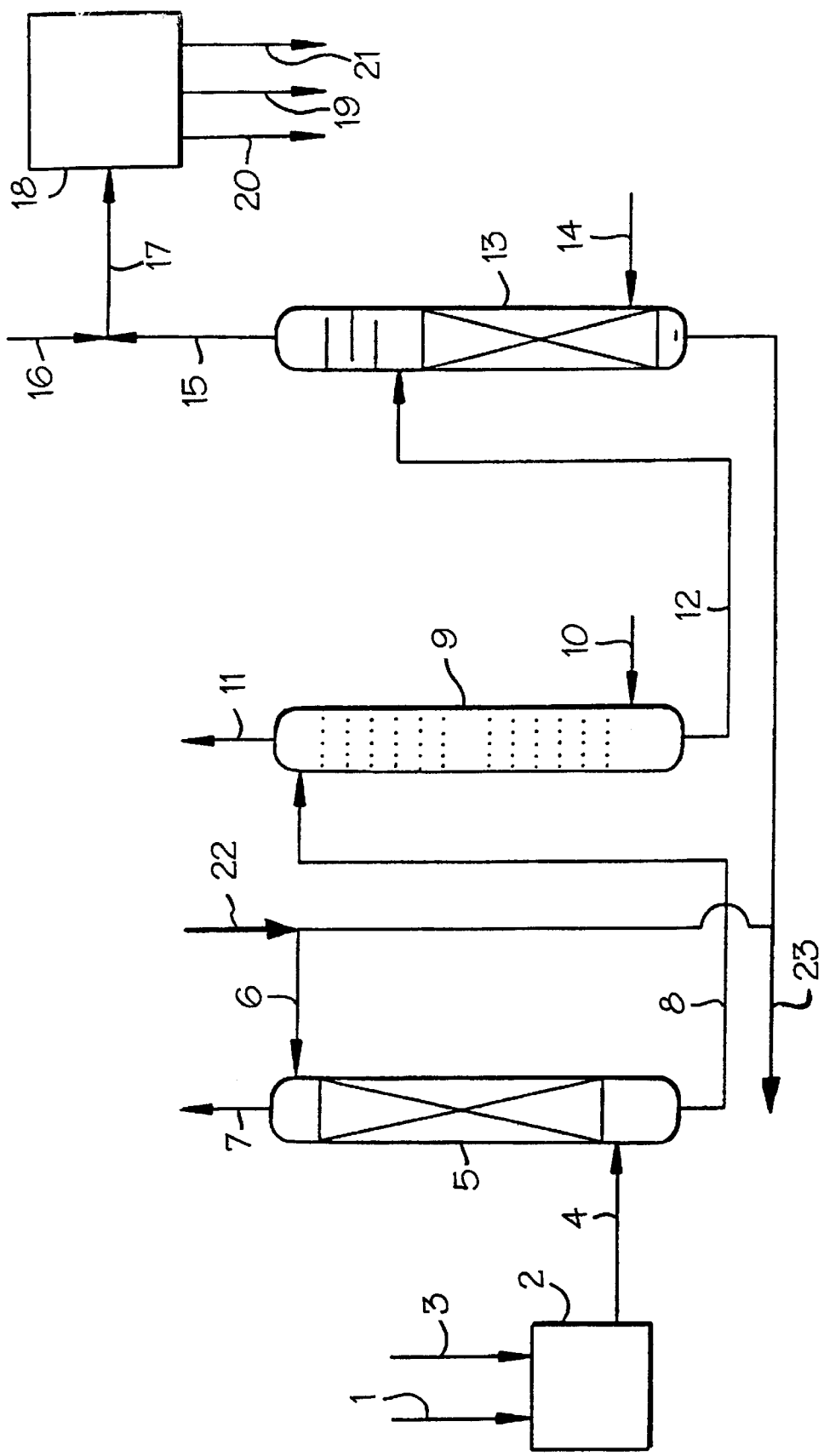

PROCESS FOR PREPARING GAMMA-BUTYROLACTONE, BUTANE-1,4-DIOL AND TETRAHYDROFURAN

This application is a 371 of PCT/GB98/03264 filed Nov. 2, 1998.

This invention relates to the production of butane-1,4-diol, γ-butyrolactone and tetrahydrofuran.

Butane-1,4-diol, together with variable amounts of γ-butyrolactone and tetrahydrofuran, can be produced by hydrogenolysis of diesters of maleic acid, fumaric acid and mixtures thereof. A major use of butane-1,4-diol is as a feedstock for the plastics industry, particularly for the production of polybutylene terephthalate. It is also used as an intermediate for the production of γ-butyrolactone and of the important solvent, tetrahydrofuran.

The maleate and fumarate diesters used as feedstock for the production of butane-1,4-diol by such a hydrogenolysis route are conveniently prepared from maleic anhydride, which is itself produced by vapour phase oxidation of a hydrocarbon feedstock, such as benzene, mixed $C_4$ olefins, or n-butane, in the presence of a partial oxidation catalyst. In the partial oxidation of benzene there is typically used a supported vanadium pentoxide catalyst promoted with $MoO_3$ and possibly other promoters. The reaction temperature is from about 400° C. to about 455° C. and the reaction pressure is from about 1 bar to about 3 bar, while about 4 times the theoretical amount of air is used in order to stay outside the explosive limits. The contact time is about 0.1 s. When the feedstock is a mixed $C_4$ olefin feedstock, i.e. a mixed butenes feedstock, then the partial oxidation catalyst may be vanadium pentoxide supported on alumina. Typical reaction conditions include use of a temperature of from about 425° C. to about 485° C. and a pressure of from about 1.70 bar to about 2.05 bar. The volume ratio of air to butenes may be about 75:1 in order to stay below explosive limits. Alternatively it is possible, according to more modern practice, to design the plant so that satisfactory safe operation can be achieved, despite the fact that the feed mixture of air and butenes is within the flammable limits. In the case of n-butane as feedstock, the catalyst is typically vanadium pentoxide and the reaction conditions include use of a temperature of from about 350° C. to about 450° C. and a pressure of from about 1 bar to about 3 bar. The air:n-butane volume ratio may be about 20:1, even though this may be within the flammable limits. One design of reactor for such partial oxidation reactions comprises vertical tubes surrounded by a jacket through which a molten salt is circulated in order to control the reaction temperature.

In each case a hot vaporous reaction mixture is recovered from the exit end of the reactor which comprises maleic anhydride vapour, water vapour, carbon oxides, oxygen, nitrogen, and other inert gases, besides organic impurities such as formic acid, acetic acid, acrylic acid, and unconverted hydrocarbon feedstock.

One way of recovering maleic anhydride from such a reaction mixture is to cool it to about 150° C. using a steam-producing stream and then to cool it further to about 60° C. by cooling it against water in order to condense part of the maleic anhydride, typically about 30% to about 60% of the maleic anhydride present. The remainder of the stream is then scrubbed with water.

Scrubbing with water or with an aqueous solution or slurry is described, for example, in U.S. Pat. No. 2,638,481. Such scrubbing results in production of a solution of maleic acid which is then dehydrated, by distilling with xylene, for example, so as to remove the water and re-form the anhydride. A disadvantage of such a procedure, however, is that an unacceptable proportion of the product remains in the vapour phase. In addition, some of the maleic acid is inevitably isomerised to fumaric acid. The byproduct fumaric acid represents a loss of valuable maleic anhydride and is difficult to recover from the process system since it tends to form crystalline masses which give rise to process problems.

Because of this isomerisation problem a variety of other anhydrous scrubbing liquids have been proposed. For example, dibutyl phthalate has been proposed as scrubbing liquid in GB-A-727828, GB-A-763339, and GB-A-768551. Use of dibutyl phthalate containing up to 10 weight % phthalic anhydride is suggested in U.S. Pat. No. 4,118,403. U.S. Pat. No. 3,818,680 teaches use of a normally liquid intramolecular carboxylic acid anhydride, such as a branched chain $C_{12-15}$-alkenyl substituted succinic anhydride, for absorption of maleic anhydride from the reaction mixture exiting the partial oxidation reactor. Tricresyl phosphate has been proposed for this purpose in FR-A-1125014. Dimethyl terephthalate is suggested for this duty in JP-A-32-8408 and dibutyl maleate in JP-A-35-7460. A high molecular weight wax as scrubbing solvent is taught in U.S. Pat. No. 3,040,059, while U.S. Pat. No. 2,893,924 proposes scrubbing with diphenylpentachloride. Use of an aromatic hydrocarbon solvent having a molecular weight between 150 and 400 and a boiling point above 140° C. at a temperature above the dew point of water in the vaporous reaction mixture, for example dibenzylbenzene, is suggested in FR-A-2285386. Absorption of maleic anhydride from the vaporous partial oxidation reaction mixture in dimethylbenzophenone followed by distillation is described in U.S. Pat. No. 3,850,758. Polymethylbenzophenones, at least a portion of which contain at least 3 methyl groups, can be used as liquid absorbent for maleic anhydride according to U.S. Pat. No. 4,071,540. Dialkyl phthalate esters having $C_4$ to $C_8$ alkyl groups and a total of 10 to 14 carbon atoms in both alkyl groups are proposed for absorption of maleic anhydride from the reaction mixture in U.S. Pat. No. 3,891,680. An ester of a cycloaliphatic acid, for example dibutyl hexahydrophthalate, is suggested as absorption solvent for maleic anhydride in ZA-A-80/1247.

It has also been proposed to effect direct condensation of maleic anhydride from the reaction mixture exiting the partial oxidation reactor. However, this procedure is inefficient because an unacceptable proportion of the maleic anhydride remains in the vapour phase.

The maleic anhydride product recovered following condensation or by scrubbing or absorption and distillation is then reacted with a suitable $C_1$ to $C_4$ alkanol, such as methanol or ethanol, to yield the corresponding di-($C_1$ to $C_4$ alkyl) maleate. This di-($C_1$ to $C_4$ alkyl) maleate may contain a minor amount of the corresponding di-($C_1$ to $C_4$ alkyl) fumarate, besides traces of the corresponding mono-($C_1$ to $C_4$ alkyl) maleate and/or fumarate. It is then subjected to hydrogenolysis to yield a mixture of butane-1,4-diol, together with variable amounts of γ-butyrolactone and tetrahydrofuran, depending upon the hydrogenolysis conditions that are selected, and of the $C_1$ to $C_4$ alkanol which can be recycled to produce further di-($C_1$ to $C_4$ alkyl) maleate.

Processes and plant for the production of dialkyl maleates from maleic anhydride are described, for example, in U.S. Pat. No. 4,795,824 and in WO-A-90/08127. This last mentioned document describes a column reactor containing a plurality of esterification trays each having a predetermined liquid hold-up and containing a charge of a solid esterification catalyst, such as an ion exchange resin containing pendant sulphonic acid groups. A liquid phase containing, for example, a carboxylic acid component flows down the column from one esterification tray to the next lower one against an upflowing stream of vapour of the lower boiling component of the esterification reagents, typically the $C_1$ to $C_4$ alkanol. Water of esterification is removed from the top of the column reactor in a vapour stream, while ester product is recovered from the sump of the reactor. As the liquid flows down the trays it encounters progressively drier reaction conditions and the esterification reaction is driven further towards 100% ester formation. This column reactor may be followed by a polishing reactor operating under liquid phase reaction conditions, the ester-containing stream from the bottom of the column reactor being admixed with further $C_1$ to $C_4$ alkanol prior to admission to the polishing reactor. When used for the production of a di-($C_1$ to $C_4$ alkyl) maleate, the column reactor can be preceded by a non-catalytic monoesterification reactor in which maleic anhydride is reacted with the $C_1$ to $C_4$ alkanol in the absence of an added catalyst to form the mono-($C_1$ to $C_4$ alkyl) maleate.

The hydrogenation of dialkyl maleates to yield butane-1,4-diol is discussed further in U.S. Pat. No. 4,584,419, U.S. Pat. No. 4,751,334 and WO-A-88/00937, the disclosures of all of which are herein incorporated by reference.

It would be desirable to simplify the production of butane-1,4,-diol, γ-butyrolactone and tetrahydrofuran, from maleic anhydride by the di-($C_1$ to $C_4$ alkyl) maleate hydrogenolysis route. In particular it would be desirable to reduce the capital cost of construction of such a plant and also to reduce its running costs, thereby making butane-1,4-diol, γ-butyrolactone and tetrahydrofuran more readily available.

It is accordingly an object of the present invention to simplify the production of butane-1,4,-diol, γ-butyrolactone and tetrahydrofuran from maleic anhydride by the di-($C_1$ to $C_4$ alkyl) maleate hydrogenolysis route. A further object is to reduce the capital cost of construction of such a plant by reducing significantly the numbers of distillation columns and the amount of other equipment required. It further seeks to reduce the running costs of a butane-1,4-diol production plant, thereby making butane-1,4-diol, γ-butyrolactone and tetrahydrofuran more readily available.

According to the present invention there is provided a process for the production of at least one $C_4$ compound selected from butane-1,4-diol, γ-butyrolactone and tetrahydrofuran, which includes the step of hydrogenation in the vapour phase of a di-($C_1$ to $C_4$ alkyl) maleate in the presence of a particulate ester hydrogenation catalyst, which process comprises:

(a) contacting a vaporous stream containing maleic anhydride vapour, water vapour, and carbon oxides in an absorption zone with a high boiling ester as solvent thereby to form a solution of maleic anhydride in the high boiling ester, said high boiling ester having a boiling point at atmospheric pressure which is at least about 30° C. higher than that of the di-($C_1$ to $C_4$ alkyl) maleate and being selected from di-($C_1$ to $C_4$ alkyl) esters of alkyl dicarboxylic acids containing up to 13 carbon atoms, mono- and di-($C_{10}$ to $C_{18}$ alkyl) esters of maleic acid, fumaric acid, succinic acid, and mixtures thereof, ($C_1$ to $C_4$ alkyl) esters of naphthalenemonocarboxylic acids, tri-($C_1$ to $C_4$ alkyl) esters of aromatic tricarboxylic acids, and di-($C_1$ to $C_4$ alkyl) esters of isophthalic acid;

(b) recovering from the absorption zone a waste gas stream;

(c) reacting maleic anhydride in the solution of maleic anhydride of step (a) under esterification conditions in an esterification zone with a $C_1$ to $C_4$ alkanol to form the corresponding di-($C_1$ to $C_4$ alkyl) maleate;

(d) recovering from the esterification zone a solution of the di-($C_1$ to $C_4$ alkyl) maleate in the high boiling ester;

(e) contacting the solution of the di-($C_1$ to $C_4$ alkyl) maleate in the high boiling ester with a gaseous stream containing hydrogen thereby to strip di-($C_1$ to $C_4$ alkyl) maleate therefrom and to form a vaporous stream comprising hydrogen and di-($C_1$ to $C_4$ alkyl) maleate;

(f) contacting material of the vaporous stream of step (e) in a hydrogenation zone under ester hydrogenation conditions with a heterogeneous ester hydrogenation catalyst thereby to convert di-($C_1$ to $C_4$ alkyl) maleate by hydrogenation to at least one $C_4$ compound selected from butane-1,4-diol, γ-butyrolactone and tetrahydrofuran; and (g) recovering from the hydrogenation zone a product stream containing said at least one $C_4$ compound.

Preferably in such a process the $C_1$ to $C_4$ alkanol is methanol or ethanol and the di-($C_1$ to $C_4$ alkyl) maleate is dimethyl maleate or diethyl maleate. The use of methanol as the $C_1$ to $C_4$ alkanol and of dimethyl maleate as the di-($C_1$ to $C_4$ alkyl) maleate is especially preferred.

The vaporous stream of step (a) of the process of the invention is preferably produced by partial oxidation of a hydrocarbon feedstock in the presence of a partial oxidation catalyst using molecular oxygen, typically in the form of air. The hydrocarbon feedstock can be benzene, or a mixed $C_4$ olefin stream, but is most preferably n-butane. The use of n-butane as hydrocarbon feedstock is currently preferred upon the grounds of cost since it is a cheaper feedstock than benzene or butenes. Hence in the process of the invention the feedstock used for production of the maleic anhydride containing vaporous stream of step (a) is most preferably n-butane and the catalyst is preferably vanadium pentoxide. Typical partial oxidation conditions in this case include use of a temperature of from about 350° C. to about 450° C. and a pressure of from about 1 bar to about 3 bar, an air to n-butane ratio of from about 15:1 to about 50:1, e.g. about 20:1 and a partial oxidation catalyst comprising vanadium pentoxide; the contact time is typically from about 0.01 s to about 0.5 s, e.g. about 0.1 s.

Partial oxidation of the hydrocarbon feedstock is conveniently conducted in a reactor which comprises vertical tubes surrounded by a jacket through which a molten salt is circulated in order to control the reaction temperature. The vaporous stream from the partial oxidation reactor can then be cooled by external cooling with boiler feed water to raise steam, and possibly also by further external cooling with cooling water to a temperature in the range of from about 60° C. to about 160° C.

In step (a) of the process of the invention the vaporous maleic anhydride stream is preferably contacted with the high boiling ester at a temperature in the range of from about 60° C. to about 160° C., preferably from about 80° C. to about 120° C., and at a pressure of from about 1 bar to about 3 bar so as to form a solution comprising maleic anhydride in the high boiling ester. The contacting can be carried out by bubbling the vaporous stream through a body of the high boiling ester. Alternatively the high boiling ester can be sprayed into the vaporous stream. Countercurrent contacting devices can also be employed wherein the ascending vaporous stream is contacted by a descending stream of high boiling ester in a gas-liquid contacting device, such as a packed scrubber tower or a scrubber tower provided with trays. In this step the high boiling ester will typically be at a lower temperature than the vaporous stream so that the latter is cooled.

In the resulting solution of maleic anhydride in the high boiling ester the concentration of maleic anhydride in the high boiling ester may range from about 100 g/l to about 400 g/l.

The high boiling ester has a boiling point at mospheric pressure that is at least about 30° C. higher, and preferably at least about 60° C. to about 70° C. higher, than that of the di-($C_1$ to $C_4$ alkyl) maleate.

As examples of esters of alkyl dicarboxylic acids containing up to 13 carbon atoms from which a suitable high boiling ester can be selected there can be mentioned dimethyl, diethyl, di-n- or -iso-propyl, di-n-, -sec-, or iso-butyl esters of suberic acid, azelaic acid, sebacic acid, undecanedioic acid, dodecanedioic acid, and tridecanedioic acid. It is preferred that the alkyl moiety in such an ester shall be derived from the same alkanol as the $C_1$ to $C_4$ alkanol used in the esterification step (c). In this way any transesterification reactions that may occur do not give rise to additional esters. Thus when the alkanol used is methanol and the dialkyl maleate is dimethyl maleate, any ester used as the high boiling ester is preferably also a dimethyl ester, such as dimethyl sebacate.

The high boiling ester may alternatively be selected from mono- and di-($C_{10}$ to $C_{18}$ alkyl) esters of one of the $C_4$ alkyl dicarboxylic acids, i.e. maleic acid, fumaric acid, and succinic acid, and mixtures thereof. Examples of such esters include the esters and mixtures thereof derived from n-decyl alcohol, lauryl alcohol, myristyl alcohol, cetyl alcohol, stearyl alcohol, and eicosanol. In this case some hydrolysis of the high boiling ester may occur in the esterification zone resulting in liberation of a minor proportion of the corresponding $C_{10}$ to $C_{18}$ alkyl alcohol. In addition some transesterification may occur in the esterification zone resulting in formation of a minor amount of a mono-($C_1$ to $C_4$ alkyl) mono-($C_{10}$ to $C_{18}$ alkyl) ester of the $C_4$ alkyl dicarboxylic acid. For example, if dilauryl maleate is used as the high boiling ester and if methanol is used as the $C_1$ to $C_4$ alkanol, then a minor amount of methyl lauryl maleate can be formed by transesterification. However, the formation of these minor byproducts is not disadvantageous even if the high boiling ester used in step (a) comprises recycled material resulting from step (e) because any free $C_{10}$ to $C_{18}$ alkanol can react with fresh maleic anhydride in step (a) to form fresh mono- or di-($C_{10}$ to $C_{18}$ alkyl) maleate. In addition any mono-($C_1$ to $C_4$ alkyl) mono-($C_{10}$ to $C_{18}$ alkyl) ester of the $C_4$ alkyl dicarboxylic acid can undergo transesterification on the next occasion that it passes through the esterification zone to form the desired solvent or the desired di-($C_1$ to $C_4$ alkyl) maleate.

The high boiling ester may alternatively be selected from ($C_1$ to $C_4$ alkyl) esters of naphthalenemonocarboxylic acids, such as methyl naphthalene-2-carboxylate, from tri-($C_1$ to $C_4$ alkyl) esters of aromatic tricarboxylic acids, such as trimethyl benzene-1,2,4-tricarboxylate, or from di-($C_1$ to $C_4$ alkyl) esters of isophthalic acid, such as dimethyl isophthalate.

The high boiling ester used in step (a) conveniently comprises material resulting from the hydrogen stripping step (e). Hence it may contain already some di-($C_1$ to $C_4$ alkyl) maleate.

Provided that appropriate conditions are adopted in step (a), the gas stream recovered in step (b) of the process of the invention can be essentially free from maleic anhydride.

Esterification of the maleic anhydride with the $C_1$ to $C_4$ alkanol is effected in step (c) in an esterification zone. This may comprise a non-catalytic reactor in which the maleic anhydride in the solution in the high boiling ester undergoes reaction in the absence of added catalyst with the $C_1$ to $C_4$ alkanol to form the corresponding mono-($C_1$ to $C_4$ alkyl) maleate. The reaction is:

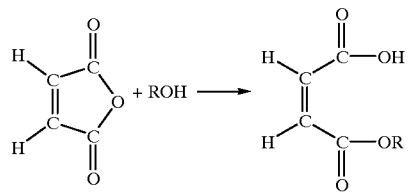

where R is a $C_1$ to $C_4$ alkyl radical. Some conversion of the mono-($C_1$ to $C_4$ alkyl) maleate to the corresponding di-($C_1$ to $C_4$ alkyl) maleate may also occur. The reaction concerned is:

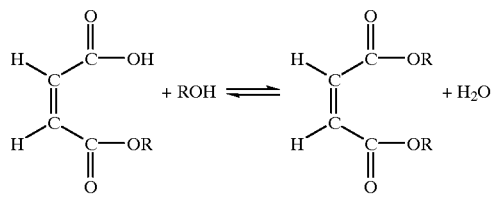

where R is as defined above.

Such a non-catalytic reactor can be operated under monoesterification conditions which typically comprise use of a temperature of from about 65° C. to about 260° C. and a pressure of from about 1 bar to about 50 bar. This can be followed by a catalytic esterification stage. For example, the catalytic esterification stage may comprise a plurality of stirred tank reactors such as is disclosed in U.S. Pat. No. 4,795,824. Preferably, however, the catalytic esterification stage comprises a column reactor of the type disclosed in WO-A-90/03127. In this case the non-catalytic monoesterification stage may comprise a stirred tank reactor or a column reactor containing one or more trays which do not contain any esterification catalyst and which is fed from the bottom with methanol or other $C_1$ to $C_4$ alkanol vapour, while the maleic anhydride solution from step (a) is fed downward through the column reactor.

If the catalytic esterification stage comprises a column reactor of the type disclosed in WO-A-90/03127, then the solution of maleic anhydride (or a solution comprising the corresponding mono-($C_1$ to $C_4$ alkyl) maleate, if a separate monoesterification stage is used) in the high boiling ester is fed to the top esterification tray of the column reactor, while an excess of $C_1$ to $C_4$ alkanol vapour is fed to the bottom of the reactor.

In the column reactor the esterification trays each hold a charge of a solid esterification catalyst. Each tray has a vapour upcomer means to permit vapour to enter the tray from below and to agitate the mixture of liquid and solid esterification catalyst in a zone of turbulence on the tray and to keep the catalyst particles in suspension. In order avoid the danger of "hot spots" forming on the tray through formation of pockets of settled catalyst particles, the floor of each tray is preferably designed so as to slope towards the zone of turbulence at a slope which exceeds the angle of repose of the catalyst particles under the liquid. In addition each esterification tray has a downcomer means which permits liquid, but not catalyst particles, to flow down from that tray to the next lower one. Such a downcomer means will usually be provided with a screen to prevent catalyst particles passing downwardly therethrough.

Typical reaction conditions in the column reactor include use of a temperature and pressure under which the $C_1$ to $C_4$ alkanol distils. Such temperature and pressure conditions will vary in dependence upon the $C_1$ to $C_4$ alkanol selected but will typically include use of a temperature of from about 65° C. to about 135° C. and a pressure of from about 1 bar to about 3 bar. A typical solid esterification catalyst is the ion exchange resin sold under the designation Amberlyst™ 16 by Rohm and Haas (U.K.) Limited of Lennig House, 2 Mason's Avenue, Croydon CR9 3NB, England or that available as DPT1 ion exchange resin from Kvaerner Process Technology Limited of The Technology Centre, Princeton Drive, Thornaby, Stockton-on-Tees TS17 6PY, England.

In passing up the column from one esterification tray to the next higher one, the upflowing $C_1$ to $C_4$ alkanol vapour carries with it water of esterification. Thus the di-($C_1$ to $C_4$ alkyl) maleate-containing liquid passing down the column reactor from one esterification tray to the next lower one encounters drier and drier conditions as it proceeds down the column. In this way the esterification reaction leading to formation of the di-($C_1$ to $C_4$ alkyl) maleate is driven further and further towards 100% conversion to the di-($C_1$ to $C_4$ alkyl) maleate.

Any byproduct acid, such as acetic acid or acrylic acid, that is also present in the vaporous stream from the partial oxidation reactor, together with any maleic acid or fumaric acid present in the solution supplied to the esterification zone, will undergo conversion to the corresponding $C_1$ to $C_4$ alkyl ester or diester, as the case may be.

The vapour phase stream emerging from the topmost esterification tray comprises $C_1$ to $C_4$ alkanol vapour and water vapour; it may further include traces of minor byproducts such as the di-($C_1$ to $C_4$ alkyl) ether, besides traces of the di-($C_1$ to $C_4$ alkyl) maleate and of the $C_1$ to $C_4$ alkyl acrylate. A further additional tray or trays may be provided above the uppermost esterification tray to act as a form of washing column in order to return di-($C_1$ to $C_4$ alkyl) maleate to the esterification trays. The resulting vapour stream, which is now essentially free from di-($C_1$ to $C_4$ alkyl) maleate, exits the top of the column.

From the bottom of the column reactor there is recovered a liquid stream comprising a solution of the di-($C_1$ to $C_4$ alkyl) maleate in the high boiling ester. This is essentially acid free. If desired this liquid can be admixed with additional $C_1$ to $C_4$ alkanol and passed through a polishing reactor containing a bed of solid esterification catalyst operating under liquid phase operating conditions. Such conditions typically include use of a temperature of from about 65° C. to about 135° C. and a pressure of from about 1 bar to about 3 bar. A typical solid esterification catalyst is the ion exchange resin sold under the designation Amberlyst™ 16 by Rohm and Haas (U.K.) Limited of Lennig House, 2 Mason's Avenue, Croydon CR9 3NB, England or that available as DPT1 ion exchange resin from Kvaerner Process Technology Limited of The Technology Centre, Princeton Drive, Thornaby, Stockton-on-Tees TS17 PY, England.

In step (e) of the process of the invention, a gas stream comprising hydrogen is passed through the solution of the di-($C_1$ to $C_4$ alkyl) maleate.

The hydrogen stripping step is preferably conducted substantially at or at a pressure slightly higher than the inlet pressure to the ester hydrogenation zone. The hydrogen stripping step is similarly preferably conducted at substantially the desired inlet temperature to the hydrogenation step or a little below this temperature, for example from about 5° C. to about 20° C. below this temperature. Then the temperature can be raised to the desired inlet temperature by admixture of further hot hydrogen-containing gas which has the additional benefit of diluting the vaporous ester-containing stream and thereby ensuring that it is at a temperature above its dew point, preferably at least about 5° C. higher than its dew point.

The hydrogenation step is advantageously conducted in the vapour phase, using a heterogeneous ester hydrogenation catalyst. Typical ester hydrogenation catalysts include reduced promoted copper catalysts, for example reduced copper chromite catalysts such as that sold under the designation PG 85/1 by Kvaerner Process Technology Limited of 20 Eastbourne Terrace, London W2 6LE.

The catalyst particles preferably have a particle size in the range of from about 0.5 mm to about 5 mm. The particles may be of any convenient shape, e.g. spheres, pellets, rings or saddles. When using a fixed bed of catalyst the reactor can be a shell-and-tube reactor, which can be operated substantially isothermally; however, it is preferably an adiabatic reactor. The use of an adiabatic reactor is advantageous since its capital cost is much lower than that of a shell-and-tube reactor and it is generally much easier to charge the reactor with the chosen catalyst.

Hydrogenation is conducted at an elevated temperature of, for example, from about 150° C. to about 240° C. and at a pressure of from about 5 bar to about 100 bar, preferably from about 50 bar to about 70 bar.

From the hydrogenation zone there is recovered a hydrogenation product mixture which contains, in addition to the $C_1$ to $C_4$ alkanol, also butane-1,4-diol, and some tetrahydrofuran and γ-butyrolactone. Even if the primary product of interest is butane-1,4-diol, the presence of these minor amounts of tetrahydrofuran and γ-butyrolactone is not disadvantageous since these compounds are important chemicals of commerce and it is accordingly economic to recover them in pure form. If desired, γ-butyrolactone can be recycled to the hydrogenation zone to produce additional butane-1,4-diol. In addition the hydrogenolysis product mixture will normally contain minor amounts of the corresponding di-($C_1$ to $C_4$ alkyl) succinate, n-butanol, the corresponding dialkyl alkoxysuccinate, e.g. dimethyl methoxysuccinate if the $C_1$ to $C_4$ alkanol is methanol, and water.

For further details regarding hydrogenation of a di-($C_1$ to $C_4$ alkyl) maleate and subsequent purification of the resultant crude hydrogenation product mixture, reference may be made to U.S. Pat. No. 4,584,419, WO-A-86/03189, WO-A-88/0937, U.S. Pat. No. 4,767,869, U.S. Pat. No. 4,945,173, U.S. Pat. No. 4,919,765, U.S. Pat. No. 5,254,758, U.S. Pat. No. 5,310,954, and WO-A-91/01960.

In order that the invention may be clearly understood and readily carried into effect a plant for the production of butane-1,4-diol, as well as some γ-butyrolactone and tetrahydrofuran, using a preferred process in accordance with the present invention will now be described, by way of example only, with reference to the accompanying drawing which is a flow diagram of the plant.

Referring to the drawing, n-butane is supplied in line 1 at a pressure of from 1 to 3 bar and at a temperature of 400° C. to a partial oxidation plant 2 which is also supplied with air in line 3. Partial oxidation plant 2 is of conventional design and includes a partial oxidation reactor comprising tubes packed with a partial oxidation catalyst consisting of vanadium pentoxide packed into tubes provided with a jacket through which molten salt can be circulated for the purpose of temperature control. The partial oxidation reactor is operated at an air:n-butane feed ratio of 20:1.

A hot vaporous partial oxidation product stream is cooled by external cooling against boiler feed water to raise steam and then against cooling water to reduce its temperature to 138° C. It is recovered from plant 2 in line 4. This contains 2.9% w/w maleic anhydride, 5.8% w/w water, 1.3% w/w carbon dioxide, 1.0% w/w carbon monoxide, 0.01 w/w acetic acid, 0.01 w/w acrylic acid, 15.7w/w oxygen, and the balance essentially comprising nitrogen and other inert gases. It is fed to the bottom of a scrubbing tower 5, up which it passes against a downflowing spray of dimethyl sebacate which is supplied at a temperature of about 68° C. from line 6. The scrubbed waste gas stream which contains 0.03% w/w maleic anhydride exits the top of scrubbing tower 5 in vent gas line 7 and is passed to a waste gas burner.

From the bottom of scrubbing tower 5 there is recovered a liquid stream in line 8 which comprises a solution of approximately 22% w/w maleic anhydride and 0.04% w/w acrylic acid in dimethyl sebacate. This is supplied to the top of a column reactor 9 of the type described in WO-A-90/08127. This comprises a number of esterification trays mounted one above the other, each containing a charge of a solid esterification catalyst, such as Amberlyst™ 16 resin or DPT1 ion exchange resin, and each having a vapour upcomer for upflowing vapour and a liquid downcomer to permit liquid to flow down the column from one esterification tray to the next lower one. Methanol vapour is supplied to the bottom of column reactor by way of line 10. Water of esterification is removed in the vapour stream exiting the column reactor in line 11. Column reactor 9 is operated at a temperature of from about 110° C. to about 125° C. and at a pressure of from about 1 bar to about 3 bar. The residence time in the column reactor is about 3 hours. Normally the temperature on the top tray will be somewhat higher (e.g. about 125° C.) than that on the lowermost tray (e.g. about 115° C.).

A solution containing about 250 g/l dimethyl maleate in dimethyl sebacate is withdrawn from the bottom of column reactor 9 in line 12 and pumped to near the top of a stripping column 13 which is operated at a temperature of 170° C. and a pressure of 885 psia (61.02 bar). Column 13 has a number of distillation trays above the point of injection of the dimethyl maleate solution into column 13 so as to reduce carryover of the high boiling ester dimethyl sebacate in the overhead stream from column 13. The solution of dimethyl maleate in dimethyl sebacate flows down stripping column 13 against an upflowing stream of hydrogen from line 14. The stripped dimethyl sebacate is recycled from the bottom of stripping column 13 by way of line 6 to the top of scrubbing tower 5. From the top of stripping column 13 there emerges in line 15 a near saturated vapour mixture stream comprising dimethyl maleate in hydrogen, with a hydrogen:dimethyl maleate molar ratio of about 320:1. This vapour mixture stream is at a temperature of from about 180° C. to about 195° C. and at a pressure of 62 bar. It is diluted with further hot hydrogen from line 16 at a temperature of from about 180° C. to about 195° C. to yield a vaporous stream with a hydrogen:dimethyl maleate molar ratio of about 350:1 and is at least about 5° C. above its dew point.

This vaporous mixture passes onwards in line 17 to hydrogenation plant 18 which includes an adiabatic reactor packed with a reduced copper-based catalyst, for example, a reduced copper chromite catalyst, and operated at an inlet temperature of 173° C., an inlet pressure of 885 psia (61.02 bar), and an exit temperature of 190° C. The dimethyl maleate feed rate corresponds to a liquid hourly space velocity of 0.5 $h^{-1}$. The plant also includes a purification section in which the crude hydrogenation product mixture is distilled in several stages to yield pure butane-1,4-diol in line 19. Lines for separate recovery of γ-butyrolactone and tetrahydrofuran are indicated at 20 and 21 respectively. Fresh dimethyl sebacate solvent can be added by means of line 22 while a purge stream of the recycled solvent stream can be taken in line 23.

The dimethyl sebacate used as solvent can be replaced by, for example, methyl naphthalene-2-carboxylate, trimethyl benzene-1,2,4-tricarboxylate or dimethyl isophthalate. Alternatively the dimethyl sebacate can be replaced as high boiling ester by a di-($C_{10}$ to $C_{18}$ alkyl) maleate, fumarate, or succinate or a mixture of two or more thereof, optionally in admixture with the corresponding mono-($C_{10}$ to $C_{18}$ alkyl) maleate, fumarate, or succinate or a mixture of two or more thereof, and/or with the corresponding free acid or mixture of acids, i.e. maleic acid, fumaric acid, and/or succinic acid. Typically the high boiling ester in such a case comprises predominantly the diester or diester mixture, with no more than a minor amount, typically less than about 5 molar % each, of the corresponding monoester or monoester mixture and/or of the corresponding acid or mixture of acids. As an example of such a high boiling ester there can be mentioned dilauryl maleate, which may contain minor amounts, preferably less than about 1 molar % each, and even more preferably less than about 0.25 molar % each, of one or more of dilauryl fumarate, dilauryl succinate, monolauryl maleate, monolauryl fumarate, monolauryl succinate, maleic acid, fumaric acid, and succinic acid. In addition, as a result of transesterification in the column reactor 9, the recycle stream in line 6 can in this case contain also a significant amount of methyl lauryl maleate, for example, up to about 10 molar & or more, typically no more than about 5 molar %, and often less than about 1 molar %; in addition it may contain minor amounts, typically less than about 1 molar % each, and even more preferably less than about 0.25 molar % each, of lauryl alcohol, methyl lauryl fumarate, and methyl lauryl succinate.

The invention is further illustrated by reference to the following Examples.

EXAMPLE 1

98.0 g of methanol and 32.0 g of maleic anhydride were allowed to react together in a round bottomed flask. To the resultant mixture was added 130 g of dimethyl sebacate and 26.0 g of DPT1 ion exchange resin. (DPT1 ion exchange resin is a macroreticular ion exchange resin containing sulphonic acid groups and is available from Kvaerner Process Technology Limited, of The Technology Centre, Princeton Drive, Thornaby, Stockton-on-Tees TS17 6PY, England). The mixture was heated to 110° C. and dry methanol fed to the flask at a rate of 6 mole $hr^{-1}$. Any unconverted methanol, together with byproduct water and dimethyl ether, was recovered overhead following condensation. The conversion of monomethyl maleate to dimethyl maleate was followed by withdrawing samples periodically from the reaction flask and analysing such samples for acid content. The experiment was continued until the level of acid dropped to less than 0.5% by weight. The results are shown in Table 1 below.

TABLE 1

| Time (minutes) | wt/wt % acid | Overheads | | |
|---|---|---|---|---|
| | | wt (g) | wt % DME | DME (g) |
| 0 | 55.9 | — | — | — |
| 30 | 18.3 | 72.5 | 0.04 | 0.03 |
| 60 | 2.9 | 114 | 0.09 | 0.14 |
| 90 | 0.41 | 94 | 0.19 | 0.31 |
| 120 | 0.27 | 101 | 0.31 | 0.62 |
| 150 | 0.12 | 110 | 0.36 | 1.02 |

Note: DME = dimethyl ether

The final sample was also analysed using a capillary gas chromatographic technique. This enabled the amount of hydrolysis of dimethyl sebacate that had occurred to be determined. The results are given in Table 2.

TABLE 2

| Component | wt/wt % |
|---|---|
| Methanol | 4.7 |
| Dimethyl sebacate | 45.8 |
| Monomethyl sebacate | 0.06 |
| Sebacic acid | 0.01 |
| Monomethyl maleate | 0.18 |
| Monomethyl fumarate | 0.14 |
| Maleic acid | 0.02 |
| Dimethyl maleate | 46.9 |
| Dimethyl fumarate | 1.91 |
| Unknowns | 0.9 |
| Water | 0.09 |

The results indicate that a small quantity of dimethyl sebacate was hydrolysed to monomethyl sebacate and sebacic acid when employing dry methanol.

EXAMPLE 2

32.0 g of maleic anhydride and 98.0 g of dry methanol were reacted together and then heated to 110° C. in 130 g of dimethyl sebacate in the presence of 26.0 g of DPT1 ion exchange resin according to the procedure of Example 1. Methanol containing 30 mol % of water was then fed to the flask in the manner described in Example 1 at a rate of 6 mole hr$^{-1}$ until the system reached equilibrium. Then the amount of water in the methanol fed to the flask was reduced to 15 mol % and the system again brought to equilibrium. The experiment was continued using methanol containing 5 mol % water and finally using dry methanol. The results obtained are set out in Table 3.

TABLE 3

| Mol % water | Product acidity | Dimethyl sebacate | Monomethyl sebacate | Sebacic acid |
|---|---|---|---|---|
| 30 | 9.76 | 43.4 | 5.0 | 0.1 |
| 15 | 4.48 | 52.0 | 2.7 | 0.1 |
| 5 | 1.27 | 42.6 | 0.5 | Trace |
| 0 | 0.16 | 59.7 | 0.2 | 0.1 |

Note: Product acidity means percentage of monomethyl maleate.

What is claimed is:

1. A process for the production of at least one $C_4$ compound selected from butane-1,4-diol, γ-butyrolactone and tetrahydrofuran, which includes the step of hydrogenation in the vapour phase of a di-($C_1$ to $C_4$ alkyl) maleate in the presence of a particulate ester hydrogenation catalyst, which process comprises:

(a) contacting a vaporous stream containing maleic anhydride vapour, water vapour, and carbon oxides in an absorption zone with a high boiling ester as solvent thereby to form a solution of maleic anhydride in the high boiling ester, said high boiling ester having a boiling point at atmospheric pressure which is at least about 30° C. higher than that of the di-($C_1$ to $C_4$ alkyl) maleate and being selected from di-($C_1$ to $C_4$ alkyl) esters of alkyl dicarboxylic acids containing up to 13 carbon atoms, mono- and di-($C_{10}$ to $C_{18}$ alkyl) esters of maleic acid, fumaric acid, succinic acid, and mixtures thereof, ($C_1$ to $C_4$ alkyl) esters of naphthalenemonocarboxylic acids, tri-($C_1$ to $C_4$ alkyl) esters of aromatic tricarboxylic acids, and di-($C_1$ to $C_4$ alkyl) esters of isophthalic acid;
   (b) recovering from the absorption zone a waste gas stream;
   (c) reacting maleic anhydride in the solution of maleic anhydride of step (a) under esterification conditions in an esterification zone with a $C_1$ to $C_4$ alkanol to form the corresponding di-($C_1$ to $C_4$ alkyl) maleate;
   (d) recovering from the esterification zone a solution of the di-($C_1$ to $C_4$ alkyl) maleate in the high boiling ester;
   (e) contacting the solution of the di-($C_1$ to $C_4$ alkyl) maleate in the high boiling ester with a gaseous stream containing hydrogen thereby to strip di-($C_1$ to $C_4$ alkyl) maleate therefrom and to form a vaporous stream comprising hydrogen and di-($C_1$ to $C_4$ alkyl) maleate;
   (f) contacting material of the vaporous stream of step (e) in a hydrogenation zone under ester hydrogenation conditions with a heterogeneous ester hydrogenation catalyst thereby to convert di-($C_1$ to $C_4$ alkyl) maleate by hydrogenation to at least one $C_4$ compound selected from butane-1,4-diol, γ-butyrolactone and tetrahydrofuran; and
   (g) recovering from the hydrogenation zone a product stream containing said at least one $C_4$ compound.

2. A process according to claim 1, in which the $C_1$ to $C_4$ alkanol is methanol and the di-($C_1$ to $C_4$ alkyl) maleate is dimethyl maleate.

3. A process according to claim 1, in which the vaporous stream of step (a) is produced by partial oxidation of a hydrocarbon feedstock in the presence of a partial oxidation catalyst using molecular oxygen.

4. A process according to claim 3, in which the hydrocarbon feedstock is n-butane.

5. A process according to claim 4, in which the partial oxidation catalyst comprises vanadium pentoxide and in which the partial oxidation conditions include use of a temperature of from about 350° C. to about 450° C., a pressure of from about 1 bar to about 3 bar, an air to n-butane ratio of from about 15:1 to about 50:1 and a contact time of from about 0.01 s to about 0.5 s.

6. A process according to claim 1, in which in step (a) the vaporous maleic anhydride stream is contacted with the high boiling ester at a temperature in the range of from about 60° C. to about 160° C. and at a pressure of from about 1 bar to about 3 bar so as to form a solution comprising maleic anhydride in the high boiling ester.

7. A process according to claim 6, in which the contacting step is carried out in a countercurrent contacting device wherein the ascending vaporous stream is contacted by a descending stream of solvent in a gas-liquid contacting device.

8. A process according to claim 1, in which the solvent is an alkyl ester whose alkyl moiety is derived from the same alkanol as the $C_1$ to $C_4$ alkanol used in the esterification step (c).

9. A process according to claim 1, in which the $C_1$ to $C_4$ alkanol is methanol, the di-($C_1$ to $C_4$ alkyl) maleate is dimethyl maleate, and the high boiling solvent is also a methyl ester.

10. A process according to claim 9, in which the methyl ester is dimethyl sebacate.

11. A process according to claim 9, in which the high boiling ester is naphthalene-2-carboxylate, trimethyl benzene-1,2,4-tricarboxylate, or dimethyl isophthalate.

12. A process according to claim 1, in which the high boiling ester comprises a di-($C_{10}$ to $C_{18}$ alkyl) ester of maleic acid, fumaric acid, succinic acid, or a mixture of two or more thereof.

13. A process according to claim 12, in which the high boiling ester further comprises a mono-($C_{10}$ to $C_{18}$ alkyl) ester of maleic acid, fumaric acid, succinic acid, or a mixture of two or more thereof.

14. A process according to claim 1, in which the high boiling ester used in step (a) comprises recycled material resulting from the hydrogen stripping step (e).

15. A process according to claim 1, in which the esterification zone comprises a non-catalytic reactor in which the maleic anhydride in the solution in the high boiling ester undergoes reaction in the absence of added catalyst with the $C_1$ to $C_4$ alkanol to form the corresponding mono-($C_1$ to $C_4$ alkyl) maleate.

16. A process according to claim 1, in which the catalytic esterification stage comprises a column reactor provided with a plurality of esterification trays each of which holds a charge of a solid esterification catalyst, has a vapour upcomer means to permit vapour to enter the tray from below and to agitate the mixture of liquid and solid esterification catalyst in a zone of turbulence on the tray and to keep the catalyst particles in suspension, and a downcomer means which permits liquid, but not catalyst particles, to flow down from that tray to the next lower one, the column reactor being supplied beneath the lowermost esterification tray with a stream of $C_1$ to $C_4$ alkanol vapour and to an upper esterification tray with a solution in the high boiling ester comprising a material selected from maleic anhydride, a mono-($C_1$ to $C_4$ alkyl) maleate wherein the $C_1$ to $C_4$ alkyl group is derived from the $C_1$ to $C_4$ alkanol, and a mixture thereof.

17. A process according to claim 16, in which the floor of each tray slopes towards the zone of turbulence at a slope which exceeds the angle of repose of the catalyst particles under the liquid.

18. A process according to claim 1, in which the esterification zone comprises an autocatalytic esterification zone wherein the esterification conditions include use of a temperature of from about 70° C. to about 250° C., a pressure of from about 1 bar to about 50 bar and wherein maleic anhydride is converted by reaction with $C_1$ to $C_4$ alkanol at least in part to the corresponding mono-($C_1$ to $C_4$ alkyl) maleate.

19. A process according to claim 1, wherein the esterification zone includes a catalytic esterification zone wherein the esterification conditions include use of a temperature of from about 65° C. to about 135° C. and of a solid esterification catalyst comprising an ion exchange resin containing pendant sulphonic acid groups.

20. A process according to claim 1, in which the hydrogen stripping step is conducted at substantially the inlet pressure to the ester hydrogenation zone.

21. A process according to claim 1, in which the hydrogen stripping step is conducted at a temperature in the range of from the inlet temperature to the hydrogenation zone to about 20° C. below the inlet temperature to the hydrogenation zone.

22. A process according to claim 1, in which the hydrogenation step is conducted in the vapour phase using a reduced promoted copper catalyst at a temperature of from about 150° C. to about 240° C. and at a pressure of from about 5 bar to about 100 bar.

23. A process according to claim 1, in which there is recovered from the hydrogenation zone a hydrogenation product mixture which contains, in addition to butane-1,4-diol and the $C_1$ to $C_4$ alkanol, also minor amounts of tetrahydrofuran and γ-butyrolactone.

24. A process according to claim 23, in which the hydrogenation product mixture is purified by distillation in one or more stages, including distillation in a "light ends" column to separate overhead the volatile components of the mixture including tetrahydrofuran, the $C_1$ to $C_4$ alkanol, water, and n-butanol.

25. A process according to claim 24, in which the bottoms product from the "light ends" column is further purified by distillation in one or more stages to yield pure butane-1,4-diol.

* * * * *